United States Patent [19]

LeFevre

[11] 4,146,028

[45] Mar. 27, 1979

[54] INTRAVENOUS SYSTEM HAVING AN ACCUMULATOR TUBE THEREIN

[75] Inventor: Robert J. LeFevre, Bethlehem, Pa.

[73] Assignee: Burron Medical Products, Inc., Bethlehem, Pa.

[21] Appl. No.: 782,412

[22] Filed: Mar. 29, 1977

[51] Int. Cl.² .................................................. A61M 5/00
[52] U.S. Cl. ...................................... 128/214 R; 128/227; 138/30
[58] Field of Search ............... 128/213, 214 R, 214 C, 128/214 E, 214 F, 214.2, 227, DIG. 3; 138/26, 30

[56] References Cited

U.S. PATENT DOCUMENTS

| 2,416,391 | 2/1947 | Hixson | 128/214 R |
| 3,228,397 | 1/1966 | Moss | 128/214 E |
| 3,601,128 | 8/1971 | Hakim | 138/30 X |
| 3,878,869 | 4/1975 | Yamanouchi et al. | 138/40 |
| 3,965,897 | 6/1976 | Lundquist | 128/214 R |

OTHER PUBLICATIONS

Campbell et al. — Surg. Aug., 1956, vol. 40, No. 2, pp. 365-370.

Primary Examiner—Dalton L. Truluck
Attorney, Agent, or Firm—Shoemaker and Mattare, Ltd.

[57] ABSTRACT

An intravenous accumulator tube for storing fluid being administered through an intravenous administration set patient includes an expansible chamber connected inline in the intravenous administration set for accumulating and storing fluid being administered when flow stoppage or restriction is encountered, whereby the stored fluid may be administered to the patient when the flow stoppage or restriction is removed.

6 Claims, 3 Drawing Figures

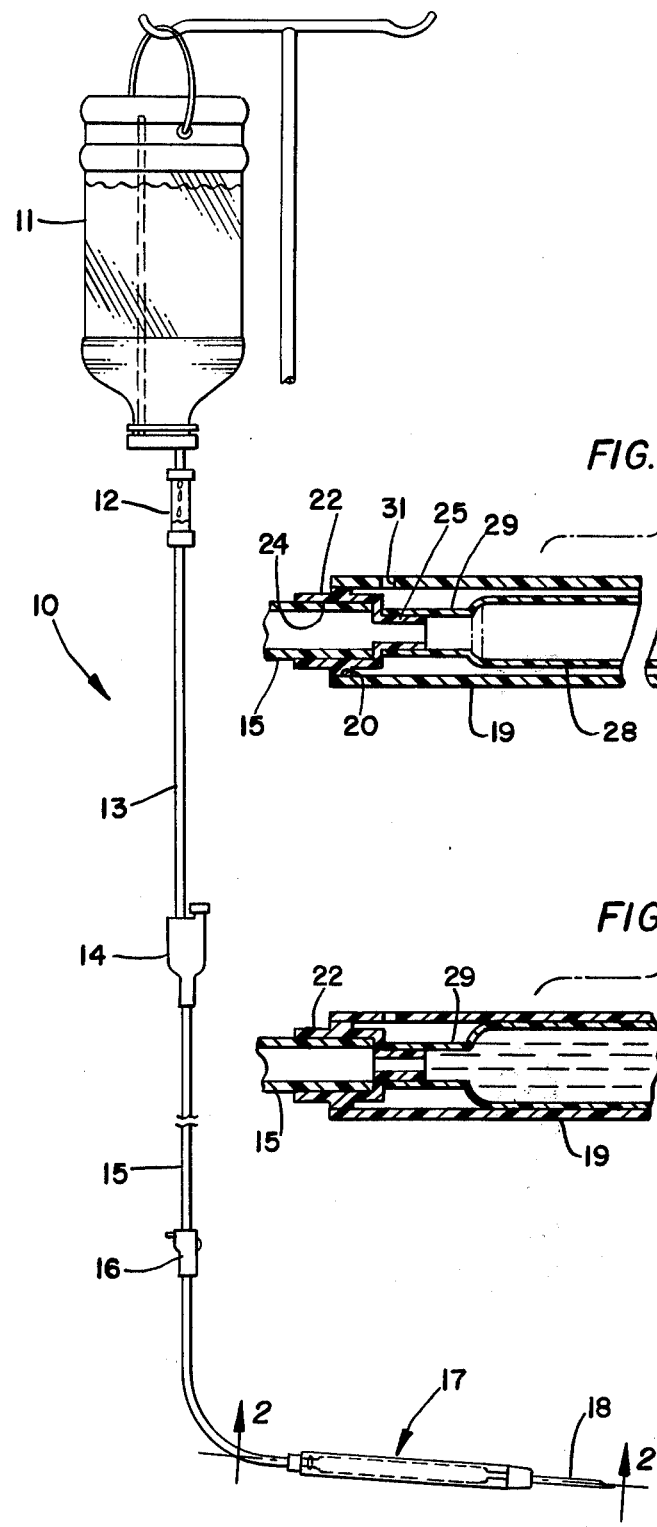
FIG. 1.
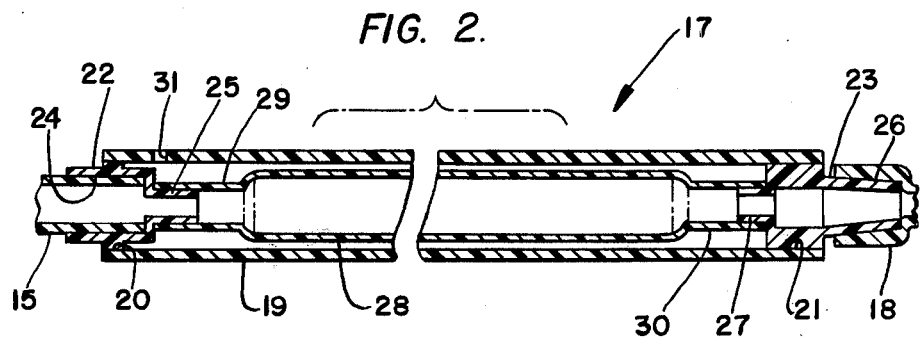
FIG. 2.
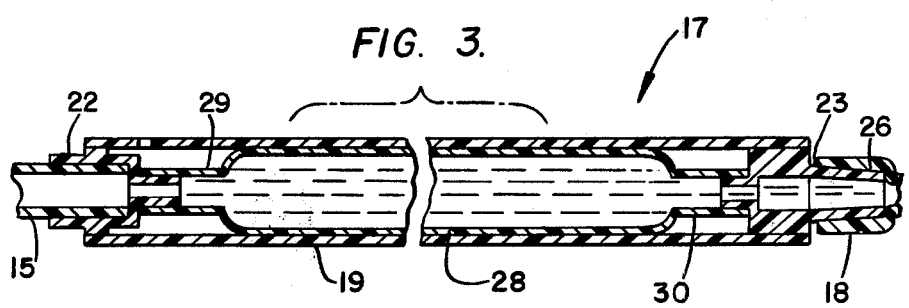
FIG. 3.
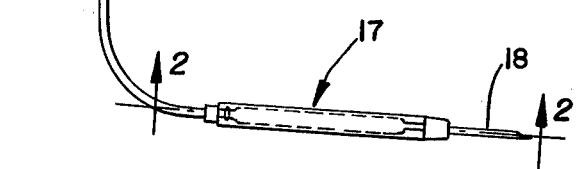

INTRAVENOUS SYSTEM HAVING AN ACCUMULATOR TUBE THEREIN

BACKGROUND OF THE INVENTION

This invention relates to intravenous administration sets, and more particularly, relates to an inline accumulator tube for use in intravenous administration sets to accumulate and store the fluid being administered when flow stoppage or restriction occurs downstream of the accumulator tube.

In gravity feed intravenous administration sets, there is a common problem of intermittent stoppage or restriction of flow of fluid through the intravenous administration set. This intermittent or temporary stoppage or restriction of flow is attributed to various factors, such as the needle or cannula pressing against the wall of the vein or rolling over of the patient or other occurrences which impose a back pressure on flow through the system resulting in a reduction of the flow rate. This momentary stoppage or slowdown of the flow reduces the intended volume of fluid to be delivered to the patient, and in many intravenous administration control means, as shown, for example, in U.S. Pat. Nos. 3,890,968, 3,790,042 and 3,655,095, this momentary blockage of flow results in an error signal being generated with the result that the control means is disrupted. This generally requires the attention of an attendant and, additionally, necessitates that the volume of fluid not delivered during the period of blockage must be made up.

The present invention provides a unique and simple solution to the problems encountered in prior art gravity feed devices. In accordance with the invention, an expansible chamber or accumulator tube is provided inline in the intravenous administration set such that a temporary blockage or restriction of flow through the set causes the fluid being delivered to expand the accumulator tube and be collected or stored therein for subsequent delivery to the patient when the blockage or restriction is removed. Thus, the invention ensures that the proper volume of fluid is delivered to a patient and prevents various electronic control means, as disclosed in the above-noted patents, for example, from entering an alarm mode when temporary blockage or stoppage occurs. In fact, the temporary blockage or restriction of flow through an intravenous administration set normally corrects itself and the accumulated fluid in the expansible chamber is delivered to the patient without requiring any action on the part of an attendant or the like. The invention thus reduces or eliminates errors in volume of fluid administered and also solves the problem of attempting to catch up with delivery of a predetermined volume of fluid when a flow blockage or restriction has occurred.

In order to ensure that an excessive volume of fluid is not stored for subsequent rapid delivery to the patient, means is provided in association with the expansible accumulator tube to limit the expanded volume thereof to a predetermined safe amount. Thus, the invention is constructed to accumulate for subsequent delivery to the patient only those amounts of fluid which would normally be missed during normal flow blockage or stoppage of a temporary nature. In other words, if the flow blockage or restriction is permanent in nature, or more serious than a temporary stoppage of the type discussed hereinabove, then once the volume of the accumulator tube has been reached, the control means controlling delivery of the intravenous fluid will enter alarm.

OBJECTS OF THE INVENTION

Accordingly, it is an object of this invention to provide an accumulator tube for use in intravenous administration sets to accumulate and store for subsequent delivery an amount of fluid which is prevented from being delivered to the patient because of a temporary blockage or restriction of flow through the intravenous administration set.

Another object of the invention is to provide an accumulator tube for use in intravenous administration sets to accumulate and store for subsequent delivery an amount of fluid being delivered to the patient, and wherein the amount accumulated and stored is limited to a predetermined maximum sufficient to accommodate an amount of fluid that would normally be blocked from delivery to a patient when a temporary blockage or restriction occurs.

BRIEF DESCRIPTION OF THE DRAWINGS

FIG. 1 is a view in elevation of an intravenous administration set embodying the accumulator tube in accordance with the invention.

FIG. 2 is a greatly enlarged fragmentary view in section taken along line 2—2 of FIG. 1 and showing the accumulator tube in a relaxed or unexpanded condition.

FIG. 3 is a view similar to FIG. 2 showing the accumulator tube in an expanded condition.

DETAILED DESCRIPTION OF THE INVENTION

In the drawings, wherein like reference numerals indicate like parts throughout the several views, an intravenous administration set of substantially conventional construction and of the gravity feed type is indicated generally at 10, and includes a source 11 of fluid to be administered to a patient, a drip chamber 12 for producing discrete drops of fluid whereby the volume of fluid being administered can be counted and controlled, and a length 13 of flexible intravenous tubing connected with a fitting 14, such as a Y-fitting or the like, and joined with a further length 15 of flexible intravenous tubing having a flow control clamp 16 mounted thereon and joined with the accumulator tube 17 of the invention. A needle or cannula 18 is joined with the other end of the accumulator tube 17 for insertion into the vein of a patient for delivery of fluid from the source 11.

As seen best in FIGS. 2 and 3, the accumulator tube 17 comprises an outer cylindrical sleeve or rigid housing 19 having opposite open ends 20 and 21 in which are respectively secured fittings 22 and 23. The fitting 22 has an inner, female Luer adaptor 24 in the outer end thereof in which the adjacent end of the length of tubing 15 is suitably secured. The inner end of fitting 22 is reduced at 25. The fitting 23, on the other hand, has an external, or male, Luer adaptor 26 on its outer end on which the needle or cannula 18 is suitably secured. The fitting 23 also has its inner end reduced as at 27. An elongate, flexible, expansible chamber or tube 28 is coaxially disposed within the rigid sleeve or housing 19 and has reduced diameter opposite end portions 29 and 30 suitably received and secured on the reduced diameter end portions 25 and 27 of the fittings 22 and 23, respectively, whereby the wall of the expansible chamber 28 is normally spaced inwardly from the inner surface of the sleeve or tube 19, as shown in FIG. 2. Further, the rigid sleeve or housing 19 has a vent opening 31 in the side wall thereof for venting the annular space defined between the expansible chamber 28 and the housing 19.

Thus, during normal flow through the system, wherein no blockage or restriction is encountered, the fluid being delivered to the patient will flow from tubing 15 into the expansible chamber 28 and thence outwardly through the needle or cannula 18 into the patient. Some very slight expansion of the accumulator tube or expansible chamber 28 may occur. In other words, the pressure of fluid within the accumulator tube or expansible chamber is balanced with atmospheric pressure and a state of equilibrium is reached. However, in the event temporary blockage or restriction of flow through the needle or cannula 18 is encountered, the expansible chamber 28 will expand into contact with the wall of tube 19, as seen in FIG. 3, thus accumulating and storing the fluid which otherwise would have been delivered to the patient. Therefore, when the temporary blockage or restriction is removed, the expansible chamber will return to its normal shape and size and the fluid will be automatically delivered to the patient without requiring any attention on the part of an attendant.

In this connection, the relative sizes of the expansible chamber 28 and the surrounding rigid housing 19 are selected such that the accumulator tube or expansible chamber 28 can only accommodate a predetermined maximum volume of fluid therein, whereby excessive delivery of fluid in a short amount of time to a patient is not possible.

For example, in a typical construction, the accumulator tube has an length of approximately 4 inches and has an inside diameter of about ¼ inch. The wall thickness of the expansible chamber or accumulator tube 28 is about 0.010 inches and the expansible chamber or tube is made of latex or other suitable material. The surrounding rigid tube or housing 19 has an inside diameter of about 0.310 inches and the expansible chamber will thus accumulate or store about 1 cc or 1 ml or the like of fluid. In other words, the capacity of the expansible chamber 28 is such that about 20 drops of fluid may be accumulated therein before an error condition is indicated.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

I claim:

1. In an intravenous administration set of the gravity flow type having a flow blockage alarm means and including a length of flexible intravenous tubing and a cannula connected therewith for insertion into the vein of a patient to deliver a fluid to the patient, the improvement comprising: means for temporarily storing a predetermined maximum volume of fluid during a temporary flow stoppage so that after removal of a temporary blockage the stored volume of fluid is delivered to a patient such that a proper volume of fluid can be delivered to a patient without actuating any alarm means associated with the intravenous administration set during such temporary fluid stoppage, said means including a housing means connected inline with the intravenous tubing, said housing means including a wall, an expansible accumulator tube connected inline with the intravenous tubing and being located within the housing means and during normal operation comprising a part of the flow path for fluid being delivered to a patient, said expansible accumulator tube being spaced radially inward from said housing means wall throughout substantially the entire length of said accumulator tubing to define an annular space, said annular space defining an expansion volume, said accumulator tubing expanding against said housing means wall throughout substantially the entire length of said accumulator tubing and accumulating a predetermined volume of fluid when flow through the cannula is blocked or restricted, so that when the blockage or restriction is removed, the accumulated volume of fluid is automatically delivered to the patient from the expanded accumulator tube, said expansion volume being sized such that the accumulator tubing will accommodate only a predetermined maximum volume of fluid therein so that excessive delivery of fluid in a short amount of time to a patient is not possible.

2. In an intravenous administration set as in claim 1, wherein said housing is rigid and tubular and surrounds the expansible accumulator tube in coaxial relation therewith.

3. In an intravenous administration set as in claim 2, wherein the accumulator tube is secured inline in the intravenous administration set immediately upstream of the cannula.

4. In an intravenous administration set as in claim 3, wherein a male Luer adaptor is secured in one end of the rigid housing and a female Luer adaptor is secured in the other end of the rigid housing, one end of the length of flexible intravenous tubing secured to the female Luer adaptor and the cannula secured to the male Luer adaptor.

5. In an intravenous administration set as in claim 4, wherein the rigid housing has a vent opening therein to vent the annular space upon expansion and contraction of the expansible accumulator tube.

6. In an intravenous administration set as in claim 2, wherein the expansible accumulator tube comprises a latex material.

* * * * *